United States Patent [19]

Isozaki et al.

[11] Patent Number: 5,750,739
[45] Date of Patent: May 12, 1998

[54] PROCESS FOR PRODUCING GLYCIDYL ESTER OF ACRYLIC ACID OR METHACRYLIC ACID

[75] Inventors: Tsuyoshi Isozaki; Masahiro Kurokawa; Akihiro Honma, all of Hiratsuka, Japan

[73] Assignee: Mitsubishi Gas Chemical Company, Inc., Tokyo, Japan

[21] Appl. No.: 687,053

[22] Filed: Aug. 7, 1996

[30] Foreign Application Priority Data

Aug. 25, 1995 [JP] Japan .................... 7-217559

[51] Int. Cl.[6] .................................. C07D 301/27
[52] U.S. Cl. .................................. 549/515
[58] Field of Search .................................. 549/515

[56] References Cited

U.S. PATENT DOCUMENTS

| | | |
|---|---|---|
| 4,755,262 | 7/1988 | Matsunaga et al. ............ 203/6 |
| 5,380,884 | 1/1995 | Hosokawa et al. ............ 549/515 |

FOREIGN PATENT DOCUMENTS

| | | |
|---|---|---|
| 0 487 305 | 5/1992 | European Pat. Off. |
| 0 519 139 | 12/1992 | European Pat. Off. |
| 0 683 163 | 11/1995 | European Pat. Off. |
| 3126943 | 3/1982 | Germany |

OTHER PUBLICATIONS

English language Abstract of JP 57–21379 and JP 57–21380 are enclosed. JP 57–21379 and JP 57–21380 are the respective 18 month publications of JP 94813/1980 and JP 94814/1980 which are identified as the priority applications claimed in DE 3126943.

*Primary Examiner*—C. Warren Ivy
*Assistant Examiner*—Garth M. Dahlen
*Attorney, Agent, or Firm*—Frishauf, Holtz, Goodman, Langer & Chick, P.C.

[57] ABSTRACT

There is disclosed a process for producing a glycidyl ester of acrylic acid or methacrylic acid which comprises the steps of neutralizing acrylic acid or methacrylic acid with a carbonate or a bicarbonate of an alkali metal in an excess amount of epichlorohydrin while an oxygen-containing gas is blown into the liquid reaction system; subjecting water formed by the neutralization and epichlorohydrin to azeotropic distillation to discharge them outside the reaction system and to form an alkali metal salt of acrylic acid or methacrylic acid; adding a quaternary ammonium salt as a catalyst to the reaction system to react the alkali metal salt of the acid with the epichlorohydrin and thus synthesize the glycidyl ester of the acid; cooling the liquid reaction product while recovering part of the excess epichlorohydrin under reduced pressure; adding aqueous solution of an alkali hydroxide to the liquid reaction product to separate into aqueous layer and organic layer; adding a catalyst deactivator to the organic phase; and subsequently distilling the organic layer to separate the glycidyl ester of the acid while blowing an oxygen-containing gas into the organic layer. The above process makes it possible to efficiently produce a highly pure glycidyl ester of acrylic acid or methacrylic acid in high yield with minimized contents of impurities.

20 Claims, No Drawings

PROCESS FOR PRODUCING GLYCIDYL ESTER OF ACRYLIC ACID OR METHACRYLIC ACID

BACKGROUND OF THE INVENTION

1. Field of the Invention The present invention relates to a process for producing a glycidyl ester of acrylic acid or methacrylic acid (hereinafter sometimes collectively referred to as "Glycidyl Methacrylate, etc.") which ester is widely used as a starting raw material for industrial use for resin modifiers, thermosetting coating materials, adhesives, textile treating agents, antistatic agents, ion exchange resins and the like.

2. Description of the Related Arts

In recent years, Glycidyl Methacrylate, etc. with a minimized content of chlorine have been required in the fields of coating materials, electronic materials, textile materials and the like from the viewpoints of coating characteristics, electrical characteristics, safety, etc.

Glycidyl Methacrylate, etc. have heretofore been produced generally by any of the following three processes.

(1) The process which comprises the steps of reacting acrylic acid or methacrylic acid (hereinafter sometimes collectively referred to as "Methacrylic Acid, etc.") with epichlorohydrin in the presence of a quaternary ammonium salt to produce a 3-chloro-2-hydroxypropyl ester of Methacrylic Acid, etc. and dehydrochlorinating the resultant ester with an alkali (refer to Japanese Patent Publication No. 34010/1971 and Japanese Patent Application Laid-Open No. 5713/1973).

(2) The process which comprises the steps of reacting Methacrylic Acid, etc. with epichlorohydrin in the presence of a quaternary ammonium salt to produce a 3-chloro-2-hydroxypropyl ester of Methacrylic Acid, etc. and subjecting the resultant ester to transesterification with an epoxy compound (refer to Japanese Patent Publication Nos. 9005/1966 and 10575/1978 and Japanese Patent Application Laid-Open No. 95216/1975).

(3) The process which comprises the steps of reacting Methacrylic acid, etc. with an alkali to produce an alkali metal salt of Methacrylic Acid, etc., subsequently reacting the resultant alkali metal salt with epichlorohydrin in the presence of a quaternary ammnonium salt and dehydrochlorinating the resulting reaction product (refer to Japanese Patent Publication Nos. 28762/1970 and 4006/1973 and Japanese Patent Application Laid-Open No. 39423/1973).

The above-mentioned processes (1) and (2) necessitate a troublesome step of treating the reaction liquid with an alkali hydroxide or like step in order to obtain Glycidyl Methacrylate, etc. in high yield and with minimized content of chlorine impurities such as a 3-chloro-2-hydroxypropyl ester of 1,3-dichloropropanol or 2,3-dichloropropanol and Methacrylic acid, etc.

On the other hand, the process (3) suffers the disadvantage of unfavorable economical efficiency in that there is a fear of causing polymerization of the alkali metal salt of Methacrylic Acid, etc. at the time of drying and so there is need for installing an expensive spray dryer or the like in order to achieve a high yield and for preparing-the aqueous solution of the alkali metal salt of Methacrylic Acid, etc. in a separate apparatus.

In order to solve such problem there is disclosed in Japanese Patent Publication Nos. 13470/1989 and 20152/1989 a process for producing a glycidyl ester of acrylic acid or methacrylic acid which comprises the steps of suspending a carbonate and/or bicarbonate of an alkali metal and Methacrylic Acid, etc. in an excess amount of epichlorohydrin to cause a neutralization reaction while air is blown thereinto; azeotropically distilling away outside the reaction system, the water formed by neutralization along with the epichlorohydrin to produce an alkali metal salt of Methacrylic Acid, etc.; subsequently adding a quaternary ammonium salt as a catalyst to the reaction system to react the alkali metal salt with the epichlorohydrin; adding water to the resulting reaction liquid after the completion of the reaction and washing the reaction liquid to separate the water layer from the organic layer; and subsequently distilling the organic layer. According to this process, it is possible to synthesize Glycidyl Methacrylate, etc. with ease in high yield.

However, in the case where the halogenated alkali and glycidol that are formed by the reaction are washed away with water, 1,3-dichloropropanol is formed in a large amount, which can not be separated from Glycidyl Methacrylate, etc. by means of distillation because of its boiling point being close to that of Glycidyl Methacrylate, etc. In addition, since a side reaction is brought about such as the formation of epichlorohydrin in the course of distillation, the Glycidyl Methacrylate, etc. to be formed as the objective product is made to contain high concentrations of epichlorohydrin and hydrolyzable chlorine, Moreover, the process suffers the drawback that the yield of Glycidyl Methacrylate, etc. is lowered by the dissolution of Glycidyl Methacrylate, etc. in the water layer and the hydrolysis of the same.

Even in the case of the alkali metal salt formed by the reaction being filtered off, impurities such as glycidol can not be removed in spite of the non-formation of 1,3-dichloropropanol and accordingly, both the resultant crude Glycidyl Methacrylate, etc. and the refined Glycidyl Methacrylate, etc. after the distillation are made to contain glycidol in a large amount. Such Glycidyl Methacrylate, etc. that contains glycidol in a large amount involves the problem that the degree of polymerization is not enhanced when it is subjected to radical polymerization, the preservation stability thereof is worsened, or the like, thereby causing deterioration of the performance when made into a coating material or resin. The above-mentioned problem necessitates an additional water washing step requiring a troublesome procedure for the purpose of removing the glycidol as disclosed in Japanese Patent Application Laid-Open No. 235980/1992, whereby the process is made industrially disadvantageous.

Further, the crude Glycidyl Methacrylate, etc. produced by any of the foregoing processes (1), (2) or (3), which is generally refined by distillation, also involves the problem that the side reactions take place in the course of distillation as represented by the reaction formulae (a), (b) and (c) (set forth hereinbelow) by the influence of the catalyst which can not be completely removed by filtration and water washing, and the by-produced epichlorohydrin, glycerol ester of methacrylic acid, glycidol and the like lower the purity and yield of the objective product.

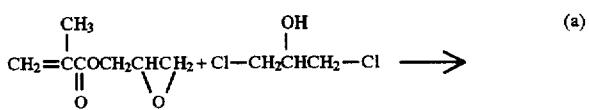
(a)

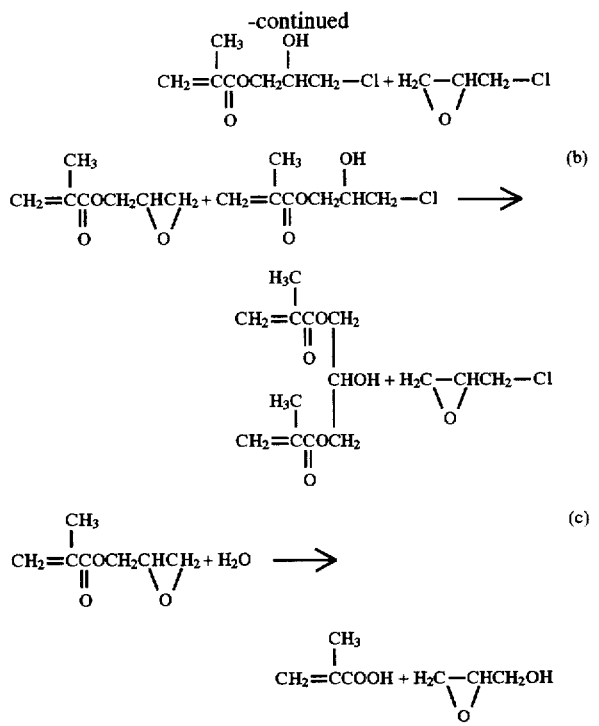

In order to solve the aforesaid problems, there are proposed a method in which a heteropolyacid or an alkali salt thereof is added to the crude Glycidyl Methacrylate, etc., followed by distillatory separation (Japanese Patent Application Laid-Open No. 255273/1988); a method in which an alkali hydroxide in powder form is added to the crude Glycidyl Methacrylate, etc., followed by distillation (Japanese Patent Application Laid-Open No. 102217/1977); a method in which the reaction liquid is subjected to stripping with an oxygen-containing gas in the presence of quaternary ammonium salt, followed by distillation (Japanese Patent Application Laid-Open No. 187682/1992); and like methods.

The Glycidyl Methacrylate, etc. that are produced by the above-mentioned process usually contain about 300 to 10,000 ppm of epichlorohydrin, about 3,000 to 20,000 ppm of glycidol and about 3,000 to 10,000 ppm of hydrolyzable chlorine. The above residual glycidol and chlorine bring about the deterioration of coating material characteristics and electrical characteristics in the fields of coating materials, electronic materials and textile materials and the problem of eruption of the skin, and in recent years the residual epichlorohydrin has caused the problems of carcinogenicity and the deterioration of working environment.

It is hoped therefore, that the impurities such as glycidol and chlorine compounds including epichlorohydrin be removed as much as possible from the Glycidyl Methacrylate, etc.

As a process for producing glycidyl methacrylate capable of suppressing the content of epichlorohydrin therein to at most 100 ppm, there is disclosed a method in which water administration is carried out at the time of the reaction of an alkali metal salt of methacrylic acid with epichlorohydrin, the resultant reaction liquid is washed with diluted aqueous solution of sodium hydroxide and distillation with steam treatment is carried out (Japanese Patent Application Laid-Open No. 2818/1995). However, this method involves the problems of necessitating water regulation within a narrow range, requiring a plurality of washing steps, causing change in the properties of initial boiling components by water and thus complicating the steps. It can not be said, therefore, that this method is an industrial method excellent in economical efficiency.

There is disclosed, as a process for producing Glycidyl Methacrylate, etc. completely free from a chlorine component, a process in which an ester of Methacrylic Acid, etc. and glycidol are subjected to transesterification (Japanese Patent Application Laid-Open Nos. 18801/1972, 11542/1980, 102575/1980 and 1780/1994). This process, however, still involves the problems of poor storage stability of glycidol, liability to polymerization of the same etc.

There is also proposed a method in which allyl methacrylate or the like is epoxidized (Japanese Patent Publication No. 6289/1972 and Japanese Patent Application Laid-Open Nos. 183275/1986, 92962/1993 and 116254/1994). There still remains therein the problems of expensive starting raw materials, increasing number of steps and unfavorable economical efficiency.

SUMMARY OF THE INVENTION

It is a general object of the present invention to provide a process for producing a highly pure glycidyl ester of acrylic acid or methacrylic acid by overcoming the various shortcomings of the foregoing prior arts.

Other objects of the present invention will become obvious from the contents of this specification hereinafter disclosed.

As a result of intensive research and investigation made by the present inventors in order to achieve the aforesaid objects, it has been found that highly pure Glycidyl Methacrylate, etc. is obtained in high yield in an economically advantageous manner which contains 300 ppm or less, preferably 200 ppm or less, more preferably 100 ppm or less of harmful epichlorohydrin; 3000 ppm or less, preferably 2000 ppm or less, more preferably 1000 ppm or less of glycidol; and 3000 ppm or less, preferably 2000 ppm or less, more preferably 1000 ppm or less of hydrolyzable chlorine through a process for producing a glycidyl ester of any of acrylic acid and methacrylic acid which comprises the steps of neutralizing any of acrylic acid and methacrylic acid and at least one member selected from the group consisting of carbonates of alkali metals and bicarbonates of the same in an excess amount of epichlorohydrin while an oxygen-containing gas is blown into the liquid reaction system; subjecting water formed by the neutralization and epichlorohydrin to azeotropic distillation to discharge them outside the reaction system and to form an alkali metal salt of any of acrylic acid and methacrylic acid; subsequently adding a queternary ammonium salt as a catalyst to the reaction system to react said alkali metal salt of said acid with the epichlorohydrin and thus synthesize the glycidyl ester of said acid; then after the completion of the esterification reaction, cooling the liquid reaction product while recovering part of the excess epichlorohydrin under reduced pressure; thereafter adding aqueous solution of an alkali hydroxide to the liquid reaction product to separate the same into aqueous layer and organic layer; adding a catalyst deactivator to the resultant organic layer and subsequently distilling the organic layer to separate the glycidyl ester of said acid while blowing an oxygen-containing gas into the organic layer.

DESCRIPTION OF PREFERRED EMBODIMENTS

The epichlorohydrin, that is, excess amount of epichlorohydrin to be used in the present is preferably selected in such an amount that it is present in the reaction system at the time of neutralization reaction and at the time of esterification reaction in a molar amount of 1 to 10 times, preferably 3 to 7 times based on Methacrylic Acid, etc. An amount thereof less than the aforesaid lower limit brings about a decrease in the yield of the product due to poor agitational property of the slurry of an alkali metal salt of Methacrylic acid etc., whereas that more than the upper limit gives rise to an increase in the amount of impurities such as chlorine and lowering in economical-efficiency.

The carbonates of alkali metals and bicarbonates of the same to be used in the present are exemplified by sodium carbonate, sodium bicarbonate, potassium carbonate and potassium bicarbonate. They are used in an amount of at least one equivalent, usually preferably 1.0 to 1.7 equivalent of Methacrylic acid, etc.

Examples of the quaternary ammonium salts to be used as a reaction catalyst include tetramethylammonium chloride, trimethylethylammonium chloride, dimethyldiethylammonium chloride, methyltriethylammonium chloride, tetraethylammonium chloride, trimethylbenzylammonium chloride and triethylbenzylammonium chloride, of which are preferably usable tetramethylammonium chloride, tetraethylammonium chloride, triethylbenzylammonium chloride and trimethylbenzylammonium chloride. The quaternary ammonium salt may be used alone or in combination with at least one other optional species. The amount of the aforesaid salt to be used is usually 0.01 to 1.5 mol % based on the Methacrylic Acid, etc.

In carrying out the process according to the present invention, it is preferable that a polymerization inhibitor be present in the reaction system in any and all of the neutralization reaction, esterification reaction and distillation. Such polymerization inhibitor may be optionally selected for use from the conventional polymerization inhibitors of amine, phenols, phosphorus, sulfur or transition-metal series. The above-mentioned esterification reaction in the present invention can be put into practice under the conventional conditions.

In the process according to the present invention, part of the excess epichlorohydrin is recovered under reduced pressure after the esterification reaction. The amount of the epichlorohydrin to be recovered is 5 to 80%, preferably 10 to 60%, more preferably 20 to 40% by weight based on the excess epichlorohydrin to be used. A recovery amount thereof less than 5% by weight results in insufficient separability between the aqueous layer and organic layer, whereas that more than 80% by weight gives rise to the problem of worsenening the slurry properties of th liquid reaction product.

As the aqueous solution of an alkali hydroxide to be added to the liquid reaction product after the completion of the esterification reaction, recitation is made of the aqueous solution of at least one alkali hydroxide selected from sodium hydroxide, potassium hydroxide, calcium hydroxide and the like. The concentration of the aqueous solution is preferably 1 to 15%, more preferably 3 to 10% by weight. The amount of the aqueous solution of the alkali hydroxide to be used therein is 50 to 500 g, preferably 100 to 400 g, more preferably 150 to 300 g per one mole of the Methacrylic Acid, etc. The temperature of the crude Glycidyl Methacrylate, etc. to which the aqueous solution of the alkali hydroxide is added, is 0° to 80° C., preferably 10° to 60° C., more preferably 20° to 40° C.

In the process according to the present invention, the aqueous solution of the alkali hydroxide is added to the liquid reaction product to separate it into the aqueous layer and organic layer, and thereafter a catalyst deactivator is added to the organic layer thus obtained. There is used, as the catalyst deactivator, at least one member selected from sodium salts and calcium salts each of alkylsulfonic acid, alkylbenzenesulfonic acid, phosphotungstic acid and phosphomolybdic acid. The amount of the catalyst deactivator to be used is 1 to 70 mol %, preferably 5 to 50 mol %, more preferably 10 to 30 mol % based on the catalyst to be used.

The oxygen-containing gas to be used in the above-mentioned reaction and distillation according to the present invention is exemplified by air and a mixture of oxygen and nitrogen, and preferably has an oxygen content of 1 to 30% by volume. The amount of the oxygen-containing gas to be used is 0.1 to 500, preferably 1 to 300, more preferably 5 to 100 milliliter (mL)/min in terms of flow rate at 20° C. under atmospheric pressure per 1 kg of Glycidyl Methacrylate, etc.

The distillation procedure in the present invention can be put into practice by optionally selecting a condition.

According to the process of the present invention, it is made possible to produce in high yield, a highly pure glycidyl ester of acrylic acid or methacrylic acid which is minimized in the contents of epichlorohydrin, glycidol and hydrolyzable chlorine.

In the following the present invention will be described in more detail with reference to comparative examples and working examples, which however shall not limit the present invention thereto.

In the working examples and comparative examples, measurements were made of the purities of the starting raw materials and the objective product by GC, and of the content of hydrolyzable chlorine by the procedure described hereunder as Reference Example 1.

In the working and comparative examples, the purities (%) of the starting raw materials and the objective product, and ppm are indicated unexceptionally by purities (% by weight), and ppm on weight basis, respectively.

REFERENCE EXAMPLE 1

(Measurement Method of the Content of Hydrolyzable Chlorine)

About one mL of sample of Glycidyl Methacrylate, etc. as the product is accurately weighed in a 100 mL Erlenmeyer flask. Then 10 mL of refined methanol and 10 mL of pure water are placed in the flask to dissolve the product. Moreover, 10 mL of 5N aqueous solution of potassium hydroxide is introduced in the flask and thereafter the flask is connected to a reflux cooler and is heated in a hot water bath (90° to 100° C.) for 30 minutes to thermally decompose the product in the flask under stirring. Then the flask is taken out from the hot water bath and allowed to cool to room temperature. After the cooling the flask is disconnected from the reflux cooler, the content in the flask is neutralized with 4N nitric acid solution after adding thereto a few drops of phenolphthalein as the indicator, followed by the addition thereof in an excess amount of one mL. After the flask is mounted to an automatic titration apparatus, the content in the flask is titrated with N/1000 silver nitrate solution. A blank measurement is simultaneously made to calculate the content of hydrolyzable chlorine by the following formula.

Content of hydrolyzable chlorine (%)=[(A−B)×N×f×3.546]/s where,

A: amount of N/1000 silver nitrate solution used in titrating the sample (mL)

B: amount of N/1000 silver nitrate solution used in titrating the blank (mL)

N: normality (0.001)

f: factor of N/1000 silver nitrate solution

S: amount of weighed sample (g)

EXAMPLE 1

A 100 liter (L) stainless steel-made reaction vessel was charged with 72.0 kg of epichlorohydrin, 5.86 kg of sodium carbonate anhydride and 0.06 kg of phenothiazine to form a liquid reactant, which was raised in temperature with air blown thereinto at a rate of 1.0 L/min. When the reaction temperature reached 110° C., 8.0 kg of methacrylic acid was added to the reactant over a period of 40 minutes. Soon after the start of the addition, the epichlorohydrin and water were azeotropically distilled out and discharged-outside the reaction system. After about 30 minutes from the end of the addition, the reaction temperature was raised to 115° C. and the azeotropic distillation almost ceased, when the azeotropic distillate was obtained including 20.43 kg of epichlorohydrin layer and 1.2 kg of aqueous layer. Subsequently 0.03 kg of tetramethylammonium chloride was added to the liquid reactant to proceed with the reaction at 115° C. for one hour, while air was continuously blown thereinto at a rate of 1.0 L/min.

After the completion of the reaction, the resultant liquid reaction product was cooled to 30° C. while a part of excess epichlorohydrin (25%) was recovered under reduced pressure and subsequently incorporated with 20 kg of 3% aqueous solution of sodium hydroxide with stirring for 5 minutes. After the stoppage of air blowing, the liquid reaction product was allowed to stand to be separated into an oil layer and an aqueous layer. The oil layer was incorporated with 0.005 kg of sodium p-toluenesulfonate as a catalyst deactivator. Thereafter, epichlorohydrin was distilled away under reduced pressure and the liquid reaction product was subjected to vacuum distillation while air was blown thereinto at a rate of 0.2 L/min. As a result, there was obtained the objective glycidyl methacrylate in an amount of 12.3 kg having 98.5% purity, 76 ppm epichlorohydrin, 900 ppm glycidol and 550 ppm hydrolyzable chlorine at 93% yield.

EXAMPLE 2

The procedure in Example 1 was repeated for the synthesis of glycidyl methacrylate except that 40 g of sodium phosphotungstate was used as a catalyst deactivator in place of sodium p-toluenesulfonate, and air was blown into during the distillation at a rate of 1 L/min instead of 0.2 L/min.

As a result, there was obtained the objective glycidyl methacrylate in a yield of 90.5%, having 99.1% purity, 55 ppm epichlorohydrin, 960 ppm glycidol and 755 ppm hydrolyzable chlorine.

EXAMPLE 3

A 100 liter (L) stainless steel-made reaction vessel was charged with 72.0 kg of epichlorohydrin, 5.86 kg of sodium carbonate anhydride and 0.06 kg of phenothiazine to form liquid reactant, which was raised in temperature with air blown thereinto at a rate of 2.0 L/min. When the reaction temperature reached 110° C., 8.0 kg of methacrylic acid was added to the reactant over a period of 30 minutes. Soon after the start of the addition, the epichlorohydrin and water were azeotropically distilled out and discharged outside the reaction system. After about 30 minutes from the end of the addition, the reaction temperature was raised to 115° C. and the azeotropic distillation almost ceased, when the azeotropic distillate was obtained including 21.64 kg of epichlorohydrin layer and 1.16 kg of aqueous layer. Subsequently 0.045 kg of tetraethylammonium chloride was added to the liquid reactant to proceed with the reaction at 115° C. for one hour, while air was continuously blown thereinto at a rate of 2.0 L/min.

After the completion of the reaction, the resultant liquid reaction product was cooled to 30° C. while a part of excess epichlorohydrin (30%) was recovered under reduced pressure and subsequently incorporated with 22 kg of 5% aqueous solution of sodium hydroxide with stirring for 5 minutes. After the stoppage of air blowing, the liquid reaction product was allowed to stand to be separated into an oil layer and an aqueous layer. The oil layer was incorporated with 0.005 kg of sodium p-toluenesulfonate as a catalyst deactivator. Thereafter, epichlorohydrin was distilled away under reduced pressure and the liquid reaction product was subjected to vaccum distillation while air was blown thereinto at a rate of 0.4 L/min. As a result, there was obtained the objective glycidyl methacrylate in an amount of 12.1 kg having 98.7% purity, 68 ppm epichlorohydrin, 950 ppm glycidol and 515 ppm hydrolyzable chlorine at 91.3% yield.

COMPARATIVE EXAMPLE 1

A 100 liter (L) stainless steel-made reaction vessel was charged with 72.0 kg of epichlorohydrin, 5.86 kg of sodium carbonate anhydride and 0.06 kg of phenothiazine to form liquid reactant, which was raised in temperature with air blown thereinto at a rate of 1.0 L/min. When the reaction temperature reached 110° C., 8.0 kg of methacrylic acid was added to the reactant over a period of 30 minutes. Soon after the start of the addition, the epichlorohydrin and water were azeotropically distilled out and discharged outside the reaction system. After about 30 minutes from the end of the addition, the reaction temperature was raised to 115° C. and the azeotropic distillation almost ceased, when the azeotropic distillate was obtained including 19.32 kg of epichlorohydrin layer and 1.12 kg of aqueous layer. Subsequently 0.03 kg of tetramethylammonium chloride was added to the liquid reactant to proceed with the reaction at 115° C. for one hour, while air was continuously blown thereinto at a rate of 1.0 L/min.

After the completion of the reaction, the resultant liquid reaction product was cooled to 30° C. while a part of excess epichlorohydrin (38%) was recovered under reduced pressure and subsequently incorporated with 22 kg of water with stirring for 5 minutes. After the stoppage of air blowing, the liquid reaction product was allowed to stand to be separated into an oil layer and an aqueous layer. The oil layer was incorporated with 0.005 kg of sodium p-toluenesulfonate as a catalyst deactivator. Thereafter, epichlorohydrin was distilled away under reduced pressure and the liquid reaction product was subjected to vaccum distillation while air was blown thereinto at a rate of 0.2 L/min. As a result, there was obtained the objective glycidyl methacrylate in an amount of 12.0 kg having 98.1% purity, 592 ppm epichlorohydrin, 650 ppm glycidol and 7200 ppm hydrolyzable chlorine at 91% yield.

COMPARATIVE EXAMPLE 2

The procedure in Example 1 was repeated for the synthesis of glycidyl methacrylate except that 40 g of sodium phosphotungstate was used as a catalyst deactivator in place of sodium p-toluenesulfonate and nitrogen was blown into during the distillation at a rate of 0.2 L/min in place of air. As a result, polymerization took place during the distillation, thereby failing to produce glycidyl methacrylate.

COMPARATIVE EXAMPLE 3

The procedure in Example 1 was repeated for the synthesis of glycidyl methacrylate except that air was not blown into at the time of the reaction. As a result, polymerization took place during the reaction, thereby failing to separate the reaction product into aqueous layer and oil layer, and produce glycidyl methacrylate.

COMPARATIVE EXAMPLE 4

The procedure in Example 3 was repeated for the synthesis of glycidyl methacrylate except that any catalyst deactivator was not added prior to the distillation. As a result, residual catalyst exerted adverse influence and thus there was obtained the objective glycidyl methacrylate in a yield of only 89.3%, having 98.2% purity, 1220 ppm epichlorohydrin, 840 ppm glycidol and 420 ppm hydrolyzable chlorine.

COMPARATIVE EXAMPLE 5

The procedure in Comparative Example 1 was repeated for the synthesis of glycidyl methacrylate except that any catalyst deactivator was not added prior to the distillation. As a result, residual catalyst exerted adverse influence and thus there was obtained the objective glycidyl methacrylate in a yield of only 86.8%, having 97.3% purity, 9400 ppm epichlorohydrin, 480 ppm glycidol and 3810 ppm hydrolyzable chlorine.

COMPARATIVE EXAMPLE 6

A 100 liter (L) stainless steel-made reaction vessel was charged with 72.0 kg of epichlorohydrin, 5.86 kg of sodium carbonate anhydride and 0.06 kg of phenothiazine to form liquid reactant, which was raised in temperature with air blown thereinto at a rate of 1.0 L/min. When the reaction temperature reached 110° C., 8.0 kg of methacrylic acid was added to the reactant over a period of 30 minutes. Soon after the start of the addition, the epichlorohydrin and water were azeotropically distilled out and discharged outside the reaction system. After about 30 minutes from the end of the addition, the reaction temperature was raised to 115° C. and the azeotropic distillation almost ceased, when the azeotropic distillate was obtained including 18.82 kg of epichlorohydrin layer and 1.22 kg of aqueous layer. Subsequently 0.03 kg of tetramethylammonium chloride was added to the liquid reactant to proceed with the reaction at 115° C. for one hour, while air was continuously blown thereinto at a rate of 1.0 L/min.

After the completion of the reaction and the stoppage of air blowing, the resultant liquid reaction product was cooled to 30° C. and subsequently filtered to remove halogenated alkali. Thereafter the filtrate was returned in the reaction vessel, and epichlorohydrin was distilled away under reduced pressure and the filtered liquid reaction product was subjected to vaccum distillation while air was blown thereinto at a rate of 0.2 L/min. As a result, there was obtained the objective glycidyl methacrylate in an amount of 11.5 kg having 97.9% purity, 3940 ppm epichlorohydrin, 16520 ppm glycidol and 6800 ppm hydrolyzable chlorine at 87.2% yield.

COMPARATIVE EXAMPLE 7

The procedure in Comparative Example 6 was repeated for the synthesis of glycidyl methacrylate except that after the filtered liquid reaction product was returned in the reaction vessel, it was incorporated with 0.005 kg of sodium p-toluenesulfonate as a catalyst deactivator and subsequently, epichlorohydrin was distilled away under reduced pressure and the liquid reaction product was subjected to vaccum distillation while air was blown thereinto at a rate of 0.2 L/min. As a result, there was obtained the objective glycidyl methacrylate in a yield of only 89.6%, having 97.2% purity, 680 pm epichlorohydrin, 19970 ppm glycidol and 3300 ppm hydrolyzable chlorine.

What is claimed is:

1. A process for producing a glycidyl ester of acrylic acid or methacrylic acid which comprises:
   (a) neutralizing acrylic acid or methacrylic acid with at least one member selected from the group consisting of a carbonate of an alkali metal and a bicarbonate of an alkali metal in an excess amount of epichlorohydrin, while an oxygen-containing gas is blown into the liquid reaction system;
   (b) carrying out an azeotropic distillation to discharge water formed by the neutralizing and epichlorohydrin, outside the liquid reaction system and forming an alkali metal salt of the acrylic acid or the methacrylic acid;
   (c) adding a quaternary ammonium salt as a catalyst to the liquid reaction system to react said alkali metal salt of said acid with the epichlorohydrin and thus synthesize the glycidyl ester of said acid in an esterification reaction;
   (d) after the esterification reaction, cooling the liquid reaction product while recovering a part of the excess epichlorohydrin under reduced pressure;
   (e) adding an aqueous solution of an alkali hydroxide to the liquid reaction product to separate out an aqueous layer and an organic layer;
   (f) adding a catalyst deactivator to the organic layer; and
   (g) distilling the organic layer to separate out the glycidyl ester of said acid, while blowing an oxygen-containing gas into the organic layer.

2. The process according to claim 1, wherein the epichlorohydrin is recovered after the completion of the esterification reaction in an amount of 5 to 80% by weight based on the excess amount of the epichlorohydrin.

3. The process according to claim 1, wherein the aqueous solution of an alkali hydroxide is an aqueous solution of at least one hydroxide selected from the group consisting of sodium hydroxide, potassium hydroxide and calcium hydroxide.

4. The process according to claim 1, wherein the aqueous solution of an alkali hydroxide has a concentration of 1 to 15% weight, and is in an amount of 50 to 500 g per one mol of the acrylic acid or the methacrylic acid.

5. The process according to claim 1, wherein the temperature of the crude glycidyl acrylate or the crude glycidyl methacrylate is in the range of 0° to 80° C. at the time of being incorporated with the aqueous solution of an alkali hydroxide.

6. The process according to claim 1, wherein the catalyst deactivator is at least one salt selected from the group consisting of a sodium salt and a calcium salt of an acid selected from the group consisting of alkylsulfonic acid, alkylbenzenesulfonic acid, phosphotungstic acid and phosphomolybdic acid.

7. The process according to claim 1, wherein the catalyst deactivator is in an amount of 1 to 70 mol % based on the amount of the catalyst.

8. The process according to claim 1, wherein the oxygen-containing gas is selected from the group consisting of air and a mixed gas of oxygen and nitrogen.

9. The process according to claim 1, wherein the oxygen-containing gas introduced during steps (b) and (h) has an oxygen content of 1 to 30% by volume, and is in an amount of 0.1 to 500 milliliter/min expressed in terms of a flow rate at 20° C. under atmospheric pressure based on 1 kg of glycidyl acrylate or glycidyl methacrylate produced by the process.

10. The process according to claim 1, wherein the glycidyl ester of acrylic acid or methacrylic acid produced by the process has a purity of at least 98% by weight, a content of epichlorohydrin of at most 300 ppm by weight, a content of glycidol of at most 3000 ppm by weight and a content of hydrolyzable chlorine of at most 3000 ppm by weight.

11. The process according to claim 2, wherein the excess amount of the epichlorohydrin is a molar amount of 1 to 10 times based on the amount of the glycidyl ester that is produced.

12. The process according to claim 11, wherein the excess amount of the epichlorohydrin is a molar amount of 3 to 7 times based on the amount of the glycidyl ester that is produced.

13. The process according to claim 12, wherein the carbonate of an alkali metal or bicarbonate of an alkali metal is selected from the group consisting of sodium carbonate, sodium bicarbonate, potassium carbonate and potassium carbonate, and is in an amount of at 1 to 1.7 equivalents of the acrylic acid or methacrylic acid.

14. The process according to claim 13, wherein the quaternary ammonium salt is selected from the group consisting of tetramethylammonium chloride, trimethylethylammonium chloride, dimethyldiethylammonium chloride, methyltriethylammonium chloride, tetraethylammonium chloride, trimethylbenzylammonium chloride and triethylbenzylammonium chloride, and is in an amount of 0.01 to 1.5 mole % based on the acrylic acid or methacrylic acid.

15. The process according to claim 14, wherein the aqueous solution of an alkali hydroxide is an aqueous solution of at least one hydroxide selected from the group consisting of sodium hydroxide, potassium hydroxide and calcium hydroxide, and is in a concentration of 3 to 10% by weight, and said aqueous solution is in an amount of 100 to 400 g per one mole of the acrylic acid or methacrylic acid.

16. The process according to claim 15, wherein the catalyst deactivator is a salt selected from the group consisting of a sodium salt and a calcium salt of an acid selected from the group consisting of alkylsulfonic acid, alkylbenzenesulfonic acid, phosphotungstic acid and phosphomolybdic acid, and the catalyst deactivator is in an amount of 5 to 50 mole % based on the amount of the catalyst.

17. The process according to claim 16, wherein the oxygen containing gas contains 1 to 30% by volume oxygen and is in an amount of 1 to 300 mL/minute in terms of a flow rate at 20° C. under atmospheric pressure per 1 kg of the glycidyl ester produced.

18. The process according to claim 17, wherein a crude glycidyl ester is produced in step (e) and is at a temperature of 10° to 60° C.

19. The process according to claim 18, wherein in step (a), the acid is acrylic acid.

20. The process according to claim 18, wherein in step (a), the acid is methacrylic acid.

* * * * *